US005654278A

United States Patent [19]
Sørensen

[11] Patent Number: 5,654,278
[45] Date of Patent: Aug. 5, 1997

[54] COMPOSITION AND METHOD COMPRISING GROWTH HORMONE AND LEUCINE

[75] Inventor: Hans Holmegaard Sørensen, Virum, Denmark

[73] Assignee: Novo Nordisk A/S, Bagsvaerd, Denmark

[21] Appl. No.: 455,886

[22] Filed: May 31, 1995

Related U.S. Application Data

[63] Continuation-in-part of Ser. No. 322,838, Oct. 13, 1994, abandoned.
[51] Int. Cl.$^6$ .................. A61K 38/00; A61K 31/195
[52] U.S. Cl. ........................... 514/21; 514/561
[58] Field of Search ........................ 514/21, 561

[56] References Cited

U.S. PATENT DOCUMENTS 4,917,658  4/1990  Viswanathan et al. .............. 604/891.1

FOREIGN PATENT DOCUMENTS

| 0 106 608 | 4/1984 | European Pat. Off. . |
| 0 303 746 A1 | 8/1987 | European Pat. Off. . |
| 0 374 120 A2 | 12/1989 | European Pat. Off. . |
| 89/09614 | 10/1989 | WIPO . |
| 93/12811 | 7/1993 | WIPO . |
| 93/12812 | 7/1993 | WIPO . |
| 93/19776 | 10/1993 | WIPO . |
| 94/03198 | 2/1994 | WIPO . |

OTHER PUBLICATIONS

Becker et al., Biotech. and Applied Biochem., vol. 9, pp. 478–487, 1987.
M. J. Kaufman, Phamaceutical Research., vol. 7, No. 3, pp. 289–293, 1990.
Gellerfors et al., Acta Pædiatr Scand [Supp], vol. 370, pp. 93–100, 1990.
Riggin et al., Analytical Biochem., vol. 167, pp. 199–209, 1987.
Houghten et al., Archives of Biochem. and Biophy., vol. 178, pp. 350–355, 1977.
Becker et al. Biotech. and Applied Biochem., vol. 10, pp. 326–337, 1988.
Teh et al, The J. of Biological Chem., vol. 262, No. 14, pp. 6472–6477, 1987.
Johnson et al., The J. of Biological Chem., vol. 264, No. 24, pp. 14262–14271, 1989.
Manning et al. Pharmaceutical Research, vol. 6, No. 11, pp. 903–918, 1989.
Wang et al., J. of Parenteral Science and Technology, vol. 42, pp. S3–S27, 1988.
Jensen et al., Biotech. and Bioengineering, vol. 36, No. 1, pp. 1–11, 1990.
Dialog accession No. 007545021, Abstract JP 63115821, 1988.

*Primary Examiner*—Kimberly Jordan
*Attorney, Agent, or Firm*—Steve T. Zelson, Esq.; Cheryl H. Agris, Esq.

[57] ABSTRACT

A pharmaceutical formulation comprising a growth hormone and leucine shows a very high stability against deamidation, oxidation and cleavage of peptide bonds. The stability of the product allows for the storing and shipment thereof in a lyophilized state or in the form of a dissolved or re-dissolved formulation at ambient temperature.

15 Claims, No Drawings

COMPOSITION AND METHOD COMPRISING GROWTH HORMONE AND LEUCINE

This application is a continuation in part of application Ser. No. 08/322,838, filed Oct. 13, 1994, now abandoned, incorporated herein by reference.

FIELD OF THE INVENTION

The present invention relates to a stabilized pharmaceutical formulation comprising growth hormone, to a method of making such formulation, and the use of leucine for stabilizing a formulation of growth hormone.

BACKGROUND OF THE INVENTION

The growth hormones from man and from the common domestic animals are proteins of approximately 191 amino acids, synthesized and secreted from the anterior lope of the pituitary gland. Human growth hormone consists of 191 amino acids. Growth hormone is a key hormone involved in the regulation of not only somatic growth, but also in the regulation of metabolism of proteins, carbohydrates and lipids. The major effect of growth hormone is to promote growth. The organ systems affected by growth hormone include the skeleton, connective tissue, muscles, and viscera such as liver, intestine, and kidneys.

Until the development of the recombinant technology and the cloning of the growth hormone gene now giving rise to production of e.g. human growth hormone (hGH) and Met-hGH in industrial scale, human growth hormone could only be obtained by extraction from the pituitary glands of human cadavers. The very limited supplies of growth hormone restricted the use thereof to longitudinal growth promotion in childhood and puberty for treatment of dwarfism, even though it has been proposed for inter alia treatment of short stature (due to growth hormone deficiency, normal short stature and Turner syndrome), growth hormone deficiency in adults, infertility, treatment of burns, wound healing, dystrophy, bone knitting, osteoporosis, diffuse gastric bleeding, and pseudoarthrosis as well as for decreasing the proportion of fat in animals to be slaughtered for human consumption.

Pharmaceutical formulations of growth hormone tend to be unstable. Degradation products such as deamidated or sulfoxylated products and dimer or polymer forms are generated—especially in solutions of growth hormone. The predominant degradation reactions of hGH are 1) deamidation by direct hydrolysis or via a cyclic succinimide intermediate to form various mounts of L-asp-hGH, L-iso-asp-hGH, D-asp-hGH, and D-iso-asp-hGH (Y.-C. J. Wang and M. A. Hanson. Parenteral Formulations of Proteins and Peptides: Stability and Stabilizers. J. Parenteral Science and Technology 42 (Suppl.) (1988) 53–525; M. C. Manning, K. Patel, R. T. Borchardt. Stability of Protein Pharmaceuticals. Pharmaceutical Research 6 (11) (1989) 903–918; and B. A. Johnson, J. M. Shirokawa, W. S. Hancock, M. W. Spellman, L. J. Basa and D. W. Asward. J. Biol. Chem. 264, 1462–71 (1989)) and 2) oxidation of the methionine residues in positions 14 and 125 (L. C. Teh et al., J. Biol. Chem., 262, 785–794 (1987); G. W. Becker et at., Biotech. Appl. Biochem., 10, 326–337 (1988); R. A. Houghten et at., Arch. Biochem. Biophys., 178, 350–355 (1977); R. M. Riggin et at., Anal. Biochem., 167, 199–209 (1987); P. Gellerfors et at., Acta Paediatr. Scand (suppl), 370, 93–100 (1990); M. J. Kaufman, Pharm. Res., 7 (3) 289–292 (1990)). The major degradation product of hGH in lyophilized state as well as in solution is deamidated hGH. Deamidation takes place to a major extent at the Asn in position 149 and to a minor extent in position 152. hGH is also rather easily oxidized in positions 14 and 125, especially in solution (L. C. Teh et al., J. Biol. Chem., 262, 785–794 (1987); G. W. Becker et at., Biotech. Appl. Biochem., 10, 326–337 (1988); R. A. Houghten et at., Arch. Biochem. Biophys., 178, 350–355 (1977); R. M. Riggin et at., Anal. Biochem., 167, 199–209 (1987); P. Gellerfors et al., Acta. Paediatr. Scand (suppl), 370, 93–100 (1990)).

The oxidation of hGH in solution forming sulfoxides is normally due to the oxygen dissolved in the formulation. The solubility of oxygen in distilled water is about 200 μM M. J. Kaufman, Pharm. Res., 7 (3) 289–292 (1990)). As the concentration of hGH in a formulation comprising 4 IU/ml is 1.3 mg/ml corresponding to 60 nM hGH, oxygen will, at normal storing conditions, be present in an excess of about 3000 times the stoichiometric amount for oxidation of hGH. It is not feasible to try to solve the problem by degassing of buffers before tapping and packing the formulations.

At present, it is not believed that these deamidated forms and oxidized forms of hGH should have toxic or altered biological activity or receptor binding properties. However, there are indications that the conformation stability of the sulfoxides is reduced as compared to native hGH.

For the development of a stable, dissolved formulation comprising hGH, it is important to know the rate of deamidation and formation of sulfoxides as well as means to control the reactions. The kinetics of degradation depend on temperature, pH and various additives or adjuvants in the hGH formulation.

Due to its instability, growth hormone is, at present, lyophilized and stored in the lyophilized form at 4° C. until it is reconstituted for use in order to minimize the degradation.

The lyophilized pharmaceutical formulations comprising hGH are, at present, reconstituted by the patient and then stored as a solution during the use for a period of up to 14 days at 4° C., during which some degradation will take place. Furthermore, the process of reconstitution of the lyophilized growth hormone tends to provide difficulties for the patient. Therefore, it is at present preferred to reconstitute the growth hormone as late as possible before use and to store and ship the formulation in a lyophilized state. The links in the distribution process from the manufacturer to the pharmacy are equipped for handling the formulations at a controlled low temperature of e.g. 4° C. which allows for a long shelf life of up to two years.

However, the extended use of pen systems for self-medication and the expanded field of use calls for a formulation which is stable for a sufficiently long time with the end user under conditions where "sufficient" cooling is not always available. Preferably, a formulation should be stable with the end user in a lyophilized state for about one month and additionally for one month in a reconstituted state in a pen device for the intended period of use of a cartridge.

Thus, there is a need for more stable formulations of growth hormone being stable in a lyophilized state or in solution at a relatively high temperature for at least about one month. Such stabilization is of very great importance when moving the administration of the growth hormone from clinics to the homes of the individuals to be treated where optimal storage may not be available as indicated above.

Furthermore, the shift in pattern of administration of growth hormone to the use of pen devices calls for a stable dissolved formulation comprising growth hormone in order to facilitate the handling to be performed by the patient. A stable dissolved formulation comprising growth hormone may be produced ready to use in the form of cartridges fitting into the pen device used by the patient who may then avoid the reconstitution of the formulation and, hence, will not have to be in the possession of a lyophilized formulation, a suitable vehicle for reconstitution as well as the necessary skill and sterile equipment for sterile reconstitution of the formulation.

For safety reasons it will also be desirable to avoid the reconstitution of a lyophilized formulation just before the use of the formulation.

Furthermore, it would also be advantageous to avoid the lyophilization step in the production of growth hormone formulations. Lyophilization is a time consuming and costly process and is also often a "bottleneck" in the production due to the limited capacity of the freeze drier. Thus, there is a need to reduce the rate of the degradation processes in order to allow for dissolved hGH formulations to be stable during shelf life and during the period of use of up to one month.

Prior attempts to stabilize hGH have not fully succeeded in preventing the formation of dimers. The problems associated with dimer formation is e.g. noted in Becker, G. W., *Biotechnology and Applied Biochemistry* 9, 478 (1987).

International Patent Publication No. WO 89/09614 and Australian patent application No. 30771/89 disclose a stable pharmaceutical formulation containing human growth hormone, glycine, and mannitol. Such a formulation shows improved stability during normal processing and storage in a lyophilized state as well as in the period of use after the reconstitution.

Published European patent application No. 303 746 discloses that animal growth hormone may be stabilized with various stabilizers to give decreased formation of insolubles and preservation of the soluble activity in aqueous environments, such stabilizers including certain polyols, amino acids, polymers of amino acids having a charged side group at physiological pH, and choline salts. Polyols are selected from the group consisting of non-reducing sugars, sugar alcohols, sugar acids, pentaerythritol, lactose, water-soluble dextrans and Ficoll; amino acids are selected from the group consisting of glycine, sarcosine, lysine or salts thereof, serine, arginine or salts thereof, betaine, N,N,-dimethyl-glycine, aspartic acid or salts thereof, glutamic acid or salts thereof; a polymer of an amino acid having a charged side group at physiological pH may be selected from polylysine, polyaspartic acid, polyglutamic acid, polyarginine, polyhistidine, polyornithine and salts thereof; and choline derivatives are selected from the group consisting of choline chloride, choline dihydrogen citrate, choline bitartrate, choline bicarbonate, tricholine citrate, choline ascorbate, choline borate, choline gluconate, choline phosphate, di(choline)sulphate and dicholine mucate.

U.S. Pat. No. 4,917,685 discloses a delivery device designed to be implanted comprising growth hormone stabilized using the same stabilizers as mentioned in EP 303746.

Published European patent application No. 374,120 discloses a stabilized formulation comprising hGH and a polyol having three hydroxy groups. Glycerol and tris (hydroxymethyl)aminomethane are mentioned. Furthermore, the presence of histidine hydrochloride as a buffer together with the polyol is disclosed.

International Patent Publication No. WO 93/12811 discloses stabilized formulations of growth hormone in the form of a lyophilized powder or an aqueous solution comprising asparagine.

International Patent Publication No. WO 93/12812 discloses stabilized formulations of growth hormone in the form of a lyophilized powder or an aqueous solution comprising histidine. In such formulations the deamidation is reduced by 25–30% as compared to a corresponding formulation of growth hormone comprising phosphate buffer.

International Patent Publication No. WO 93/19776 discloses protein formulations comprising growth hormone comprising citrate as buffer substance being more stable than formulations comprising phosphate buffer. The formulations may also comprise amino acids such as glycine and alanine and/or mannitol or other sugar alcohols and/or glycerol and/or other carbohydrates and optionally a preservative such as benzyl alcohol.

International Patent Publication No. WO 94/03198 discloses a stable aqueous formulation containing human growth hormone, a buffer, a non-ionic surfactant, and, optionally, a neutral salt, mannitol, or, a preservative.

SUMMARY OF THE INVENTION

It has now surprisingly been found that a formulation of human growth hormone comprising leucine as additive shows a very high stability against deamidation and oxidation. The stability of the product allows for the storing and shipment thereof in a lyophilized state or in the form of a dissolved or re-dissolved formulation. The invention is related to such a formulation. Additionally, the invention is related to a method for making such a formulation comprising adding the growth hormone to a solution comprising leucine. The invention is also directed to a method for treating a disorder associated with growth hormone deficiency, comprising administering the pharmaceutical formulation of claim 7 in an amount effective to treat said deficiency.

DETAILED DESCRIPTION OF THE INVENTION

The pharmaceutical formulations of the invention may be formulated for administration in any suitable way, e.g. by parenteral or oral administration or administration to a mucosal membrane, e.g. nasal administration. The pharmaceutical formulation may be presented in the form of a dose in a vial or cartridge or any other suitable container such as a prefilled syringe or a pen device.

Thus, the formulation of the invention may be in the form of a lyophilized powder to be reconstituted later using conventional vehicles such as distilled water or water for injection or in the form of a solution comprising growth hormone. Such vehicles may comprise conventional preservatives such as m-cresol and benzyl alcohol.

A preferred embodiment of the invention is in the form of a pharmaceutical formulation of human growth hormone comprising leucine and further comprising a carrier in the form of a buffered aqueous solution of growth hormone. Such a formulation is in a ready-to-use form and may be stored and shipped as an aqueous solution without any considerable degradation.

The pharmaceutical formulation of the invention may furthermore comprise salts for adjusting the tonicity and/or an excipient in order to facilitate the processing thereof, e.g. lyophilization and the rapid and complete dissolution of a lyophilized formulation when reconstituting the formulation before use. An excipient may be selected from disaccharides such as lactose, trehalose, and sucrose, sugar alcohols such as sorbitol or mannitol, polysaccharides such as the polymers commercialized as Dextran® products such as Dextran® 40, Dextran® 70 or Dextran® 75, and Ficoll® and polyvalent alcohols such as polyethylene glycol or polyvinyl alcohol or a combination of two or more of these.

The pharmaceutical formulation may be prepared by adding growth hormone to a solution comprising leucine, preferably in an amount of up to 100 mM, more preferred in an amount of about 1–10 mM, preferably 2–6 mM, most preferred about 3–5 mM. The growth hormone may be in solid form or may be in a buffer solution, e.g. histidine, citrate, tartrate or phosphate buffer. The leucine solution may be obtained by dissolving leucine in deionized water optionally containing of benzyl alcohol. The pH of said formulation may be adjusted from about 2 to about 8 more preferred to pH from 5 to 7, especially to about 6.8 by adding an acid which has no adverse effect on the growth hormone, preferably a physiologically acceptable acid e.g. a mineral acid such as hydrochloric acid, sulphuric acid or nitric acid or an organic acid such as acetic acid. In one embodiment of the method of the invention, salts and/or an excipient may be added. In yet another embodiment, the solution is filled into a container and lyophilized.

Still another aspect of the invention relates to the use of leucine for the formulation of a stabilized formulation of growth hormone.

In the present context "growth hormone" may be growth hormone from any origin such as arian, bovine, equine, human, bovine, porcine, salmon, trout or tuna growth hormone, preferably bovine, human or porcine growth hormone, human growth hormone being most preferred. The growth hormone used in accordance with the invention may be native growth hormone isolated from a natural source, e.g. by extracting pituitary glands in a conventional manner, or a growth hormone produced by recombinant techniques, e.g. as described in E. B. Jensen and S. Carlsen in Biotech and Bioeng. 36, 1–11 (1990). The "growth hormone" may also be a medicated form of growth hormone wherein one or more amino acid residues has (have) been deleted; an analogue thereof wherein one or more amino acid residues in the native molecule has (have) been substituted by another amino acid residue, preferably a natural amino acid residue, as long as the substitution does not have any adverse effect such as antigenicity or reduced action; or a derivative thereof, e.g. having an N- or C-terminal extension such as Met-hGH. The preferred growth hormone is hGH.

The term "dose" of growth hormone refers to that amount that provides therapeutic effect in an administration regimen. The formulations hereof are prepared containing amounts of hGH at least about 0.1 mg/ml, preferably upwards of about 10 mg/ml, preferably from about 1 mg/ml to about 40 mg/ml, more preferably from about 1 mg/ml to about 25 mg/ml, e.g. from 1 mg/ml to about 5 mg/ml, calculated on the ready-to-use formulation. For use of these compositions in administration to human beings suffering from hypopituitary dwarfism, for example, these formulations contain from about 0.1 mg/ml to about 10 mg/ml, corresponding to the currently contemplated dosage regimen for the intended treatment. The concentration range is not critical to the invention and may be varied by the physician supervising the administration.

Leucine to be used in accordance with the present invention is preferably naturally occurring alpha leucine. The amino acid(s) may be l or d amino acid(s) or a mixture thereof.

In the present context "high stability" is obtained when the formulation is more stable than the conventional formulation comprising phosphate buffer and preferably as stable as a corresponding formulation comprising histidine as a stabilizer in which the de-amidation of hGH is reduced by approximately 20% as compared with phosphate buffer as disclosed in WO 93/12812.

The solvent used in the formulations of the invention may be water, alcohols such as ethyl, n-propyl or isopropyl, butyl alcohol or mixtures thereof. The solvent may comprise a preservative such as m-cresol or benzyl alcohol.

EXAMPLE

Reduction of the deamidation.

The rate of deamidation was examined at 37° C. for hGH formulations comprising 4 mg/ml hGH at pH 6.8 in the presence of 5 mM L-leucine or D-leucine as compared to histidine at pH 6.8.

The hGH formulations were prepared by dissolving 8 mg hGH in 2 ml of 10 mM solution of the amino acid. Thus, 2 ml 3.0% of benzyl alcohol was added to give a final formulation of 4 mg/ml hGH, 5 mM D- or L-leucine or histidine, 1.5% benzyl alcohol, pH 6.8 (adjusted adding HCl or NaOH).

The hGH formulations stated in the below table were stored at 37° C. for 7 days and analyzed for the content of deamidated hGH by IE-HPLC. The results appear from the below table.

TABLE

| Formulation | pH start/pH end/% desamido | Corrected content of deamidated hGH* | Contents of desamido hGH as compared with His |
|---|---|---|---|
| L-leucine | 6.7/6.6/15.3 | 16.8 | 97 |
| D-leucine | 6.7/6.7/16.6 | 17.6 | 102 |
| Histidine | 6.7/6.8/16.8 | 17.3 | 100 |

*Desamido corrected by 1% per 0.1 pH unit deviation from 6.8

The contents of deamidated hGH in the starting material was: 2.0%

From the above table it appears that the deamidation of hGH is reduced by 25–30% by addition of D-leucine or L-leucine as compared with phosphate buffer (at least as stable as compared to histidine, cf. WO 93/12812 above).

The above results show that the rate of deamidation is reduced in solutions containing L-leucine or D-leucine in a low concentration of up to 100 mM, preferably about 5 mM. The rate of deamidation may be reduced by more than 30% by substituting the phosphate buffer with L-leucine or D-leucine.

The use of benzyl alcohol as preservative seems to have no influence on the rate of deamidation.

What is claimed is:

1. A pharmaceutical formulation comprising a growth hormone and leucine.

2. The pharmaceutical formulation according to claim 1 in which said formulation is in the form of a buffered aqueous solution.

3. The pharmaceutical formulation according to claim 1 in which the formulation has a pH from about 2 to about 8.

4. The pharmaceutical formulation according to claim 1 wherein the concentration of leucine is up to about 100 mM.

5. The pharmaceutical formulation according to claim 1 further comprising salts and saccharides.

6. The pharmaceutical formulation according to claim 1 wherein the growth hormone is hGH.

7. The pharmaceutical formulation according to claim 1 in which said formulation is in lyophilized form.

8. A method of preparing the pharmaceutical formulation of claim 1 comprising adding the growth hormone to a solution comprising leucine.

9. The method according to claim 8 in which the solution comprising leucine is obtained by dissolving leucine in deionized water.

10. The method according to claim 8 in which the solution comprising leucine also comprises benzyl alcohol.

11. The method according to claim 8 in which further comprises adjusting the pH of said formulation to from about 2 to about 8.

12. The method according to claim 8 which further comprises adding salts.

13. The method according to claim 8 which further comprises adding an excipient.

14. The method according to claim 8 which further comprises filling a solution comprising growth hormone and leucine into a container and lyophilizing said solution.

15. A method for treating a disorder in a patient affectable by growth hormone comprising administering to the patient an amount of the pharmaceutical formulation of claim 1 effective to treat said disorder.

* * * * *